(12) United States Patent
Kiyose et al.

(10) Patent No.: US 10,524,764 B2
(45) Date of Patent: Jan. 7, 2020

(54) ULTRASONIC DEVICE, ULTRASONIC PROBE, ELECTRONIC EQUIPMENT, AND ULTRASONIC IMAGE DEVICE

(71) Applicant: SEIKO EPSON CORPORATION, Tokyo (JP)

(72) Inventors: Kanechika Kiyose, Nagano (JP); Hironori Suzuki, Nagano (JP); Hiroshi Matsuda, Gifu (JP)

(73) Assignee: Seiko Epson Corporation, Tokyo (JP)

( * ) Notice: Subject to any disclaimer, the term of this patent is extended or adjusted under 35 U.S.C. 154(b) by 1115 days.

(21) Appl. No.: 14/499,841

(22) Filed: Sep. 29, 2014

(65) Prior Publication Data

US 2015/0094590 A1 Apr. 2, 2015

(30) Foreign Application Priority Data

Sep. 30, 2013 (JP) .................................. 2013-203476

(51) Int. Cl.
| | |
|---|---|
| *A61B 8/00* | (2006.01) |
| *H01L 41/332* | (2013.01) |
| *H01L 41/08* | (2006.01) |
| *H01L 27/20* | (2006.01) |
| *B06B 1/06* | (2006.01) |

(52) U.S. Cl.
CPC .......... *A61B 8/4488* (2013.01); *B06B 1/0629* (2013.01); *H01L 27/20* (2013.01); *H01L 41/081* (2013.01); *H01L 41/332* (2013.01); *A61B 8/4427* (2013.01)

(58) Field of Classification Search
CPC ......... B06B 1/0629; B06B 1/06; H01L 27/20; H01L 41/332; H01L 41/081; H01L 41/053; A61B 8/4488; A61B 8/4427; A61B 8/14; A61B 8/00
USPC .......................................... 600/447; 310/334
See application file for complete search history.

(56) References Cited

U.S. PATENT DOCUMENTS

| | | | | |
|---|---|---|---|---|
| 6,457,361 | B1 * | 10/2002 | Takeuchi ................ | G01G 3/13 435/287.2 |
| 2003/0141783 | A1 * | 7/2003 | Klee ..................... | B06B 1/0622 310/324 |
| 2003/0156163 | A1 * | 8/2003 | Watanabe ............. | B41J 2/14233 347/68 |

(Continued)

FOREIGN PATENT DOCUMENTS

| | | |
|---|---|---|
| JP | 2005-051688 A | 2/2005 |
| JP | 2007-235795 A | 9/2007 |

(Continued)

*Primary Examiner* — Sanjay Cattungal
(74) *Attorney, Agent, or Firm* — Global IP Counselors, LLP

(57) ABSTRACT

An ultrasonic device includes a base, a plurality of ultrasonic transducer elements, and a reinforcing body. The base defines a plurality of openings arranged in an array form. The ultrasonic transducer elements are arranged respectively corresponding to the openings with a plurality of vibration films being respectively provided for the ultrasonic transducer elements. The reinforcing body is fixed to the base in an area between adjacent ones of the vibration films when viewed in a plan view along a thickness direction of the base. The reinforcing body has Young's modulus greater than Young's modulus of the base.

16 Claims, 10 Drawing Sheets

(56) References Cited

U.S. PATENT DOCUMENTS

| | | | |
|---|---|---|---|
| 2006/0186759 A1* | 8/2006 | Kim | H03H 3/02 310/320 |
| 2008/0116765 A1* | 5/2008 | Sugiura | B06B 1/0629 310/334 |
| 2009/0178260 A1* | 7/2009 | Yamazaki | H03H 3/04 29/25.35 |
| 2009/0301200 A1* | 12/2009 | Tanaka | B06B 1/0292 73/603 |
| 2010/0277040 A1* | 11/2010 | Klee | B06B 1/0292 310/324 |
| 2013/0223191 A1 | 8/2013 | Nakamura et al. | |
| 2013/0258802 A1 | 10/2013 | Nakamura et al. | |
| 2013/0338507 A1* | 12/2013 | Onishi | B06B 1/0622 600/459 |
| 2014/0042870 A1* | 2/2014 | Ohashi | H03H 3/08 310/313 R |
| 2015/0094590 A1* | 4/2015 | Kiyose | B06B 1/0629 600/447 |
| 2015/0298172 A1 | 10/2015 | Nakamura et al. | |
| 2017/0136497 A1 | 5/2017 | Nakamura et al. | |

FOREIGN PATENT DOCUMENTS

| | | |
|---|---|---|
| JP | 2013-175879 A | 9/2013 |
| JP | 2013-211604 A | 10/2013 |
| JP | 2013-255692 A | 12/2013 |

* cited by examiner

ULTRASONIC DEVICE, ULTRASONIC PROBE, ELECTRONIC EQUIPMENT, AND ULTRASONIC IMAGE DEVICE

CROSS-REFERENCE TO RELATED APPLICATIONS

This application claims priority to Japanese Patent Application No. 2013-203476 filed on Sep. 30, 2013. The entire disclosure of Japanese Patent Application No. 2013-203476 is hereby incorporated herein by reference.

BACKGROUND

1. Technical Field

The present invention relates to an ultrasonic device, ultrasonic probe, electronic equipment, and ultrasonic image device or the like using the same.

2. Related Art

Ultrasonic devices are generally known. For example, with the ultrasonic device noted in Japanese Laid-Open Patent Publication No. 2005-51688, a base has a plurality of openings. The openings are arranged in array form. An ultrasonic transducer element is arranged for each opening. Each ultrasonic transducer element has a vibration film. A piezoelectric body and electrode are formed on the vibration film. Ultrasonic waves are emitted according to the ultrasonic vibration of the vibration film.

SUMMARY

Crosstalk of the ultrasonic waves occurs during ultrasonic vibration of the vibration films. The ultrasonic vibration of the vibration film is conveyed through the base and propagated in the adjacent vibration films. For preventing this kind of crosstalk, for example with Japanese Laid-Open Patent Publication No. 2007-235795, the piezoelectric body is segmented. However, when segmenting between vibration films with the ultrasonic device noted in Japanese Laid-Open Patent Publication No. 2005-51688, there is a marked weakening of support strength of the vibration film. If trying to ensure support strength, it is difficult to have higher density of the ultrasonic transducer elements.

With at least one aspect of the present invention, it is possible to provide an ultrasonic device for which it is possible to prevent crosstalk well by making the base strength great while realizing higher density of the ultrasonic transducer elements.

(1) An ultrasonic device according to one aspect includes a base, a plurality of ultrasonic transducer elements, and a reinforcing body. The base defines a plurality of openings arranged in an array form. The ultrasonic transducer elements are arranged respectively corresponding to the openings with a plurality of vibration films being respectively provided for the ultrasonic transducer elements. The reinforcing body is fixed to the base in an area between adjacent ones of the vibration films when viewed in a plan view along a thickness direction of the base. The reinforcing body has Young's modulus greater than Young's modulus of the base.

When sending ultrasonic waves, the vibration film of the ultrasonic transducer element does ultrasonic vibration. Ultrasonic wave signals are emitted according to the ultrasonic vibration. At this time, the base forms a frame body enclosing the opening for each individual opening. A reinforcing body is overlapped on the frame body to form a composite body. The bending rigidity of the composite body exceeds the bending rigidity of the frame body alone. The rigidity of the frame body is increased. Wobbling of the frame body during ultrasonic vibration of the vibration film is suppressed. In this way, crosstalk of ultrasonic waves during ultrasonic vibration of one vibration film is prevented. As a result, it is possible for the ultrasonic transducer elements to be arranged at high density. On the other hand, when the frame body rigidity is low, there is distortion of the frame body during ultrasonic vibration of the vibration film, and crosstalk of the ultrasonic waves from one vibration film toward the adjacent vibration films occurs.

(2) The reinforcing body, in cooperation with the base, preferably forms a composite body having a second moment of area greater than a second moment of area of the base alone. The bending rigidity is specified by the product of the Young's modulus and the second moment of area. If the second moment of area of the composite body is greater than the second moment of area of the base alone, the bending rigidity will increase. The reinforcing body is able to effectively reinforce the bending rigidity.

(3) The reinforcing body preferably has a crossing part along a first direction and a second direction that cross each other in the plan view. The rigidity of the reinforcing body is increased by the reinforcing bodies crossing each other. The bending rigidity of the base is further increased.

(4) A crossing angle of the first direction and the second direction is preferably 90 degrees. The bending rigidity of the base is reliably increased.

(5) In the plan view, the reinforcing body preferably has a first straight line part cutting across an array area of the ultrasonic transducer elements in the first direction. In this way, the base rigidity is increased for the entire array area.

(6) The reinforcing body preferably has an additional crossing part spaced apart from the crossing part in the second direction for each group of the ultrasonic transducer elements connected in common to one signal line among the ultrasonic transducer elements. The vibration films belonging to the group of ultrasonic transducer elements connected in common to one signal line vibrate simultaneously according to the supply of drive signals. The group of ultrasonic transducer elements that vibrate simultaneously forms one segment. The reinforcing body is interrupted for each segment, so transmission of the ultrasonic vibration between segments by conveyance through the reinforcing body is prevented. Ultrasonic wave crosstalk is reduced.

(7) The reinforcing body preferably further includes a first straight line part positioned in an area between the crossing part and the additional crossing part in the plan view, and an auxiliary reinforcing body part extending along the second direction. Even when the reinforcing body is segmented, the segmented area is reinforced by the auxiliary reinforcing body part. Despite segmenting of the reinforcing body, rigidity is ensured by the work of the auxiliary reinforcing body part.

(8) The reinforcing body preferably has a second straight line part cutting across the array area of the ultrasonic transducer elements in the second direction in the plan view. In this way, the rigidity of the base is increased for the entire array area.

(9) The reinforcing body preferably has an additional crossing part spaced apart from the crossing part in the first direction for each group of the ultrasonic transducer elements connected in common to one signal line among the ultrasonic transducer elements. The vibration films belonging to the group of ultrasonic transducer elements connected in common to one signal line vibrate simultaneously according to the supply of drive signals. The group of ultrasonic transducer elements vibrating simultaneously forms one segment. Since the reinforcing body is interrupted for each segment, the transmission of ultrasonic vibration between segments conveyed through the reinforcing body is prevented. Crosstalk of ultrasonic waves is reduced. The segments are arranged in array form.

(10) The ultrasonic device preferably further includes: a first conductive film extending in a first direction in common to the ultrasonic transducer elements; a piezoelectric film disposed on the first conductive film for each of the ultrasonic transducer elements; a second conductive film extending in a second direction in common to the ultrasonic transducer elements; and an insulating film separating the first conductive film from the second conductive film on the piezoelectric film, the insulating film being continuous from the reinforcing body. The reinforcing body is preferably made of an insulating material. The first conductive film and the second conductive film are mutually separated on the piezoelectric film. A space in contact with the piezoelectric film is formed between the first conductive film and the second conductive film on the surface of the piezoelectric film. The space is occupied by the insulating film. The insulating film prevents the entry of moisture into the space. As a result, even if the ultrasonic device is exposed to moisture, it is possible to avoid electrical shorting between the first conductive film and the second conductive film.

(11) The ultrasonic device preferably further includes an additional second conductive film extending in the second direction. The first conductive film preferably has a film thickness greater than a film thickness of the second conductive film between the second conductive film and the additional second conductive film. Since sufficient film thickness is ensured for the first conductive film, it is possible to avoid an increase in wiring resistance. Therefore, it is possible to sufficiently ensure ultrasonic wave detection sensitivity.

(12) It is possible to use the ultrasonic device incorporated in a probe. The probe can be equipped with the ultrasonic device, and a case supporting the ultrasonic device.

(13) It is possible to use the ultrasonic device incorporated in electronic equipment. The electronic equipment can be equipped with the ultrasonic device, and a processing device connected to the ultrasonic device, and configured to process the output of the ultrasonic device.

(14) It is possible to use the ultrasonic device incorporated in an ultrasonic image device. The ultrasonic image device can be equipped with the ultrasonic device, and a display device configured to display an image generated based on the output of the ultrasonic device.

BRIEF DESCRIPTION OF THE DRAWINGS

Referring now to the attached drawings which form a part of this original disclosure.

DETAILED DESCRIPTION OF EXEMPLARY EMBODIMENTS

Hereafter, an embodiment of the present invention while referring to the attached drawings will be described. This embodiment described hereafter does not unduly limit the contents of the present invention noted in the scope of patent claims, and all of the structures described with this embodiment are not absolutely necessary as means for solving of the present invention.

(1) Overall Configuration of the Ultrasonic Diagnostic Device

Figure 1:
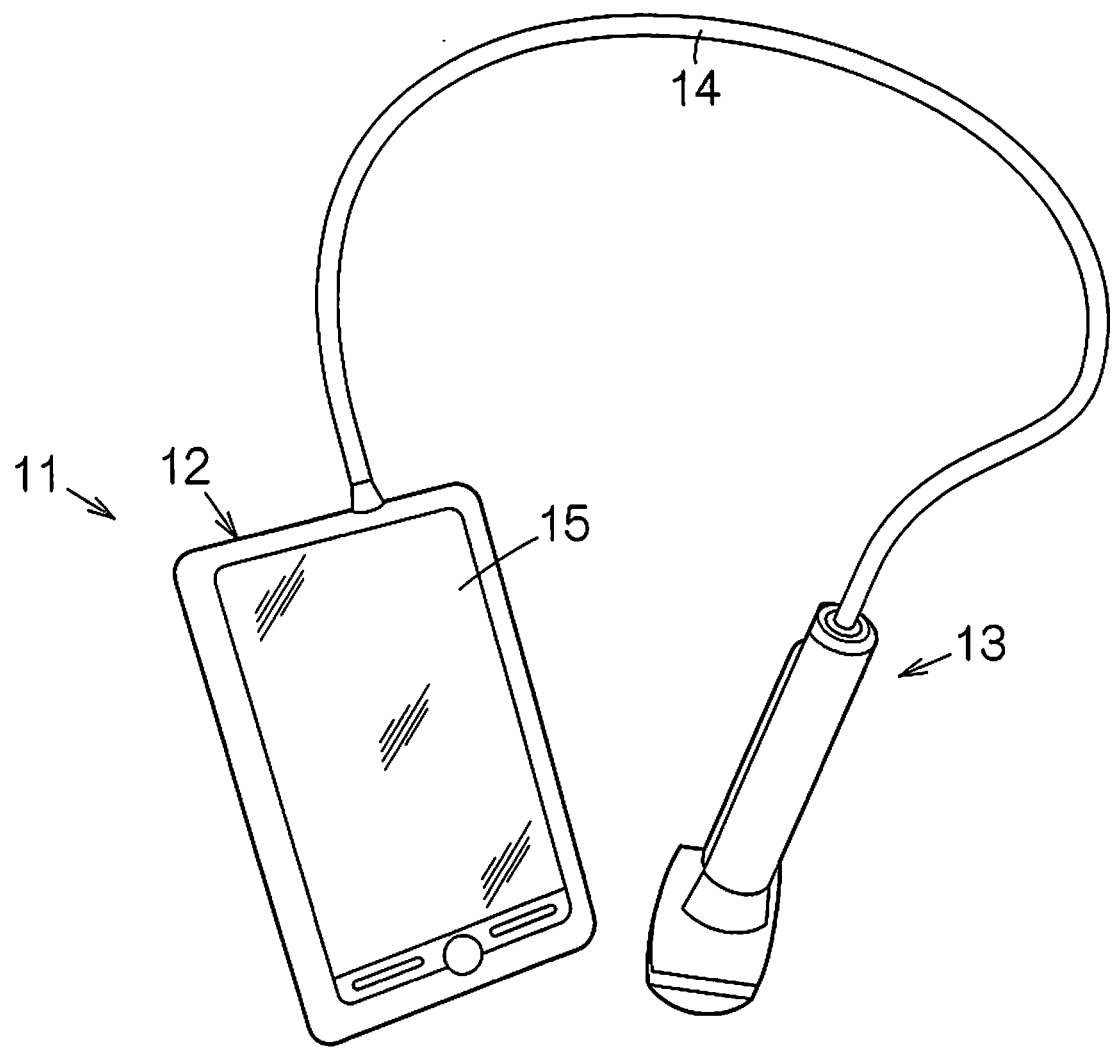
FIG. 1 is an external view schematically showing an ultrasonic diagnostic device as an example of an electronic equipment.

FIG. 1 schematically shows a specific example of electronic equipment, specifically, the configuration of an ultrasonic diagnostic device (ultrasonic image device) 11. The ultrasonic diagnostic device 11 is equipped with a device terminal (processing device) 12 and an ultrasonic probe (probe) 13. The device terminal 12 and the ultrasonic probe 13 are connected to each other by a cable 14. The device terminal 12 and the ultrasonic probe 13 exchange electronic signals through the cable 14. A display panel (display device) 15 is incorporated in the device terminal 12. The screen of the display panel 15 is exposed on the surface of the device terminal 12. With the device terminal 12, an image is generated based on the ultrasonic waves detected by the ultrasonic probe 13. The detected results put into image form are displayed on the screen of the display panel 15.

Figure 2:
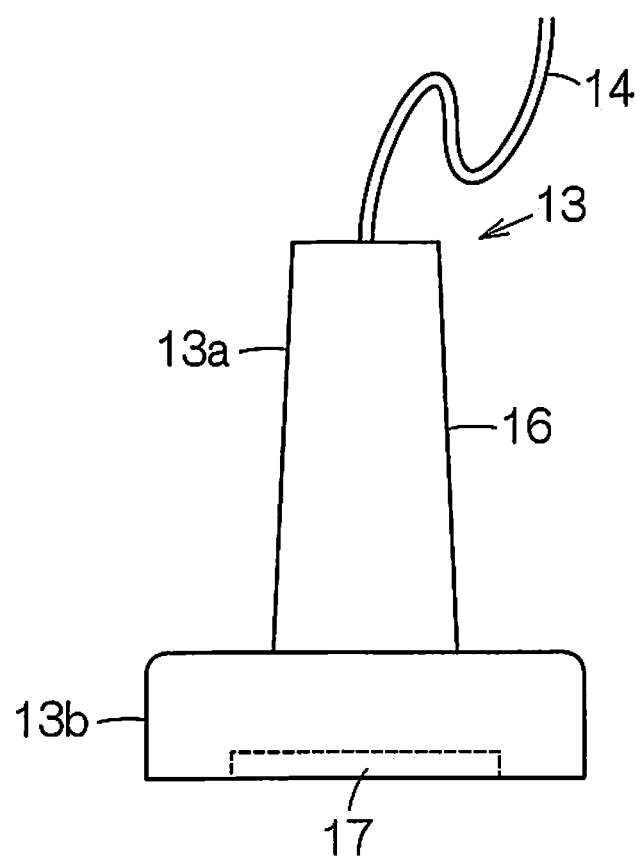
FIG. 2 is an enlarged front view of the ultrasonic probe.

As shown in FIG. 2, the ultrasonic probe 13 has a case 16. Inside the case 16 is housed an ultrasonic transducer element unit (hereafter called "element unit") 17. The surface of the element unit (ultrasonic device) 17 can be exposed on the surface of the case 16. The element unit 17 outputs ultrasonic waves from the surface and receives reflected waves of the ultrasonic waves. In addition, the ultrasonic probe 13 can be equipped with a probe head 13b linked so as to be feely detachable with a probe main unit 13a. At this time, the element unit 17 can be incorporated inside the case 16 of the probe head 13b.

Figure 3:
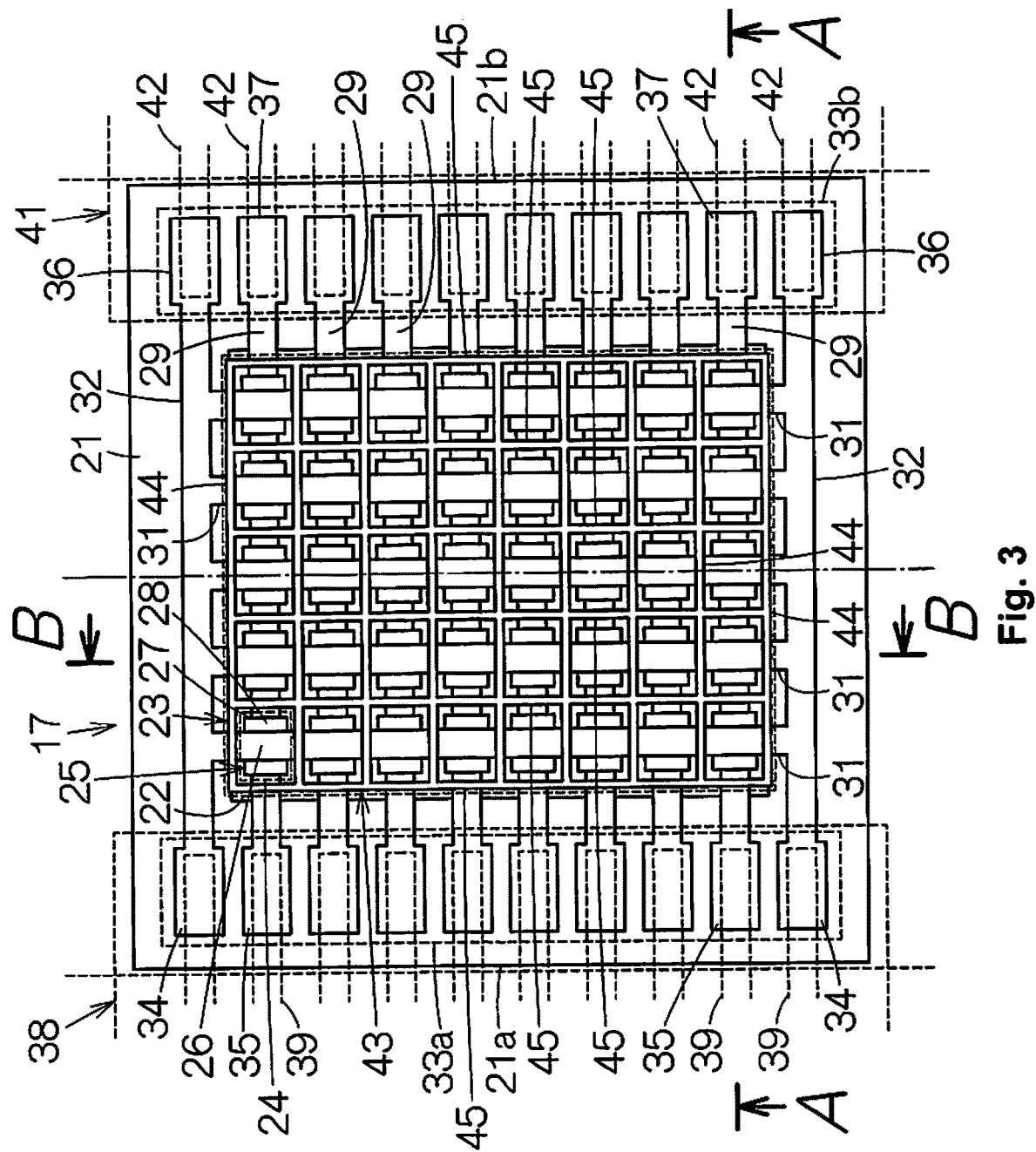
FIG. 3 is an enlarged plan view of the ultrasonic transducer element unit of the first embodiment.

FIG. 3 schematically shows a plan view of the element unit 17 of the first embodiment. The element unit 17 is equipped with a base 21. An element array 22 is formed on the base 21. The element array 22 is constituted with an array of ultrasonic transducer elements (hereafter called "elements") 23. The array is formed in a matrix of a plurality of columns and a plurality of rows. In addition, it is possible to establish a zigzag arrangement for the array. With a zigzag arrangement, the even numbered Xrow element 23 group can be skewed by a column pitch of ½ in relation to the odd numbered Xrow element 23 group. The number of elements of one of the odd numbered Xrow and the even numbered Xrow can be one less than the number of elements of the other.

Each individual element 23 is equipped with a vibration film 24. Details of the vibration film 24 will be described later. FIG. 3 depicts the outline of the vibration film 24 with a dotted line with a plan view in the direction orthogonal to the film surface of the vibration film 24 (substrate thickness direction plan view). The inner side of the outline correlates to the interior of the area of the vibration film 24. The outside of the outline correlates to outside the area of the vibration film 24. A piezoelectric element 25 is formed on the top of the vibration film 24. As described later, with the piezoelectric element 25, a piezoelectric film 28 is sandwiched between an upper electrode 26 and a lower electrode 27. These are overlapped in sequence. The element unit 17 is constituted as one ultrasonic transducer element chip.

A plurality of first conductive films 29 are formed on the surface of the base 21. The first conductive films 29 extend mutually in parallel to the Xrow direction of the array. One first conductive film 29 is allocated per Xrow of elements 23. One first conductive film 29 is arranged in common with elements 23 aligned in the Xrow direction of the array. The first conductive film 29 has the lower electrode 27 formed for each individual element 23. In this way, the first conductive film 29 is arranged both inside the area and outside the area of the vibration film 24. For example, titanium (Ti), iridium (Ir), or a laminated film of titanium (Ti) and platinum (Pt) can be can be used for the first conductive film 29. However, it is also possible to use other conductive materials for the first conductive film 29.

A plurality of second conductive films 31 are formed on the surface of the base 21. The second conductive films 31 extend mutually in parallel to the column direction of the array. One second conductive film 31 is allocated for each column of elements 23. One second conductive film 31 is connected in common to elements 23 aligned in the column direction of the array. The second conductive film 31 has the upper electrode 26 formed for each individual element 23. Both ends of the second conductive film 31 are respectively connected to a pair of lead-out wires 32. The lead-out wires 32 extend mutually in parallel in the row direction of the array. Therefore, all of the second conductive films 31 have the same length. In this way, the upper electrodes 26 are connected in common to the elements 23 of the entire matrix. In this way, the second conductive films 31 are arranged on the inside area and outside area of the vibration film 24. The second conductive films 31 can be formed using iridium (Ir), for example. Other conductors can also be used for the second conductive films 31.

The energization of the elements 23 can be switched for each Xrow. Linear scanning or sector scanning is realized according to this energization switching. Since one Xrow of elements 23 output ultrasonic waves simultaneously, it is possible to determine the number of the elements 23 in one row, in other words, the number of columns of the array, according to the ultrasonic wave output level. The number of columns can be set to approximately 10 to 15 columns, for example. This is abbreviated in the drawing with five columns depicted. The number of Xrows of the array can be determined according to the expansion of the scan range. The number of Xrows can be set to 128 Xrows or 256 Xrows, for example. This is abbreviated in the drawing with eight Xrows depicted. The role of the upper electrodes 26 and the lower electrodes 27 can also be interchanged. Specifically, while the lower electrodes are connected in common to the elements 23 of the entire matrix, the upper electrodes can be connected in common to each Xrow of the array.

The outline of the base 21 has a first side 21a and a second side 21b facing opposite, partitioned by a pair of straight lines that are mutually parallel. One line of first terminal arrays 33a is arranged between the first side 21a and the element array 22 outline. One line of second terminal arrays 33b is arranged between the second side 21b and the element array 22 outline. The first terminal arrays 33a can be formed in one line in parallel to the first side 21a. The second terminal arrays 33b can be formed in one line in parallel to the second side 21b. The first terminal array 33a is constituted by one pair of upper electrode terminals 34 and a plurality of lower electrode terminals 35. Similarly, the second terminal array 33b is constituted by a pair of upper electrode terminals 36 and a plurality of lower electrode terminals 37. The upper electrode terminals 34 and 36 are respectively connected to both ends of one lead-out wire 32. The lead-out wire 32 and the upper electrode terminals 34 and 36 can be formed plane-symmetrically at the perpendicular plane that bisects the element array 22. The lower electrode terminals 35 and 37 are respectively connected to both ends of one second conductive film 31. The second conductive film 31 and the lower electrode terminals 35 and 37 can be formed plane-symmetrically at the perpendicular plane that bisects the element array 22. Here, the outline of the base 21 is formed as a rectangle. The outline of the base 21 can also be square or can be a trapezoid.

A first flexible printed wiring board (hereafter called "first wiring board") 38 is coupled to the base 21. The first wiring board 38 is covered by the first terminal array 33a. A conductive line, specifically a first signal line 39, corresponding individually to the upper electrode terminal 34 and the lower electrode terminal 35, is formed on one end of the first wiring board 38. The first signal line 39 is bonded separately facing to individually match the upper electrode terminal 34 and the lower electrode terminal 35. Similarly, a second flexible printed wiring board (hereafter called "second wiring board") 41 is covered on the base 21. The second wiring board 41 is covered by the second terminal array 33b. A conductive line, specifically, a second signal line 42, is formed corresponding individually to the upper electrode terminal 36 and the lower electrode terminal 37 at one end of the second wiring board 41. The second signal line 42 is bonded separately facing to individually match the upper electrode terminal 36 and the lower electrode terminal 37.

A grid form reinforcing body 43 is fixed on the surface of the base 21. The reinforcing body 43 is overlapped on the surface of the base 21. The reinforcing body 43 is equipped with a plurality of first elongated pieces (first straight line parts) 44 extending in the Xrow direction of the element array 22 (first direction), and a plurality of second elongated pieces (second straight line parts) 45 extending in the column direction of the element array 22 (second direction). Each of the first elongated pieces 44 has a shape that cuts across the area of the element array 22 completely in the Xrow direction. Each of the second elongated pieces 45 has a shape that cuts across the area of the element array 22 completely in the column direction. The first elongated pieces 44 and the second elongated pieces 45 form a crossing part crossing each other at a crossing angle of 90 degrees. The first elongated pieces 44 are arranged in parallel to each other. The second elongated pieces 45 are arranged in parallel to each other. The first elongated pieces 44 and the second elongated pieces 45 are arranged at positions skewed from the elements 23 in the parallel direction to the surface of the base 21. One Xrow of the elements 23 are arranged between adjacent first elongated pieces 44. One column of the elements 23 are arranged between adjacent second elongated pieces 45. The reinforcing body 43 is formed from an insulating material such as alumina ($Al_2O_3$) or zirconium oxide ($ZrO_2$) for example. The alumina or zirconium oxide has a greater Young's modulus than that of silicon or silicon oxide. The reinforcing body 43 can be formed using photolithography technology, for example.

Figure 4:
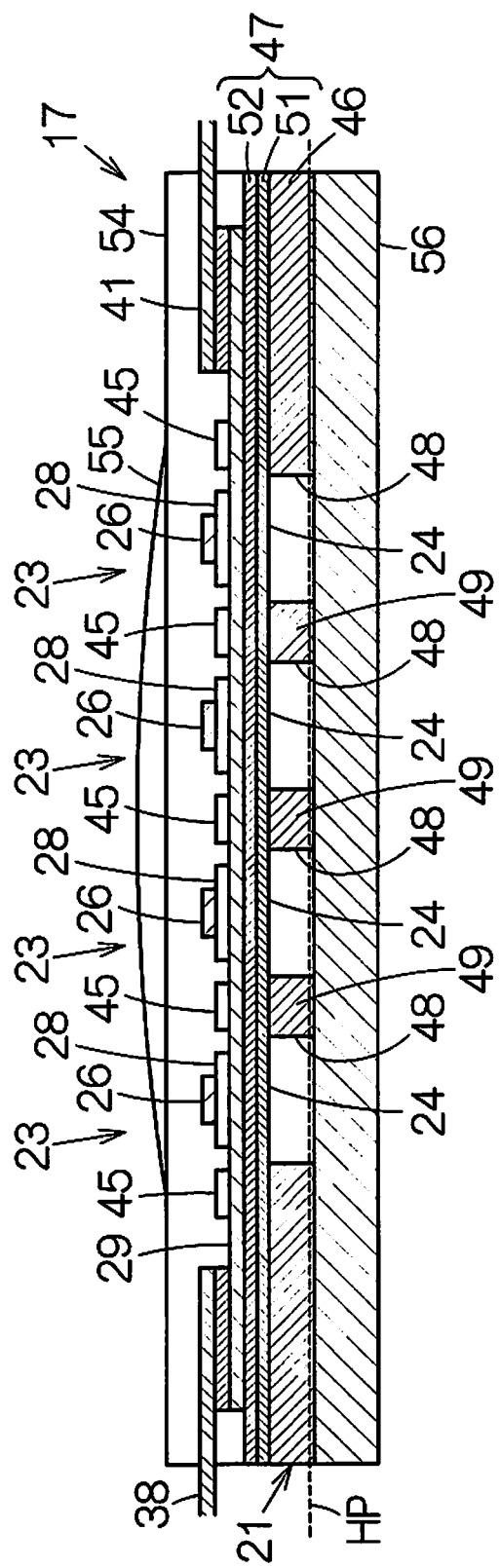
FIG. 4 is a cross section view along line A-A of FIG. 3.

As shown in FIG. 4, the base 21 is equipped with a main unit 46 and a flexible film 47. The flexible film 47 is formed over the entire surface on the surface of the main unit 46. The main unit 46 is formed from silicon (Si), for example. An opening 48 is formed on each individual element 23 on the main unit 46. The openings 48 are arranged in array form on the main unit 46. The outline of the area in which the openings 48 are arranged correlates to the outline of the element array 22. A partition wall 49 is demarcated between two adjacent openings 48. Adjacent openings 48 are partitioned by the partition wall 49. The wall thickness of the partition wall 49 correlates to the gap between the openings 48. The partition wall 49 defines two wall surfaces within the plane mutually expanding in parallel. The wall thickness correlates to the distance between two wall surfaces. Specifically, the wall thickness can be regulated by the length of the perpendicular line sandwiched between the wall surfaces orthogonal to the wall surface.

The flexible film 47 is constituted by a silicon oxide ($SiO_2$) layer 51 laminated on the surface of the main unit 46, and a zirconium oxide ($ZrO_2$) layer 52 laminated on the surface of the silicon oxide layer 51. The flexible film 47 is in contact with the opening 48. In this way, a portion of the flexible film 47 corresponding to the outline of the opening 48 forms the vibration film 24. Of the flexible film 47, the vibration film 24 is the part for which it is possible to do film vibration in the thickness direction of the main unit 46 since it faces the opening 48. The film thickness of the silicon oxide layer 51 can be determined based on the resonance frequency.

The reinforcing body 43 (second elongated piece 45) is overlapped on the surface of the flexible film 47 on the partition wall 49. The second elongated piece 45 is overlapped on the partition wall 49 that functions as a girder or beam to form a composite body. Depending on the overlapping, the composite body can have a second moment of area (a moment of inertia of plane area) greater than the second moment of area of the base 21 alone. Here, with the composite body, the bending rigidity is increased in the direction orthogonal to the surface of the base 21.

On the surface of the vibration film 24 are laminated in sequence the first conductive film 29, the piezoelectric film 28, and the second conductive film 31. The piezoelectric film 28 can be formed using lead zircon titanate (PZT), for example. It is also possible to use another piezoelectric material for the piezoelectric film 28. The piezoelectric film 28 covers at least a portion of the lower electrode 27 and a portion of the vibration film 24. The upper electrode 26 covers at least a portion of the piezoelectric film 28. Here, the piezoelectric film 28 completely covers the surface of the first conductive film 29 below the second conductive film 31. It is possible to avoid shorting between the first conductive film 29 and the second conductive film 31 by working of the piezoelectric film 28.

An acoustic adjustment layer 54 is laminated on the surface of the base 21. The acoustic adjustment layer 54 can be cover the surface of the base 21 over the entire surface, for example. As a result, the element array 22, the first and second terminal arrays 33a and 33b, and the first and second wiring boards 38 and 41 are covered by the acoustic adjustment layer 54. The acoustic adjustment layer 54 is adhered to the surface of the element 23. It is possible to use a silicone resin film for the acoustic adjustment layer 54, for example. The acoustic adjustment layer 54 protects the element array 22 structure, the first terminal array 33a and the first wiring board 38 junction, and the second terminal array 33b and the second wiring board 41 junction.

An acoustic lens 55 is laminated on the acoustic adjustment layer 54. The acoustic lens 55 is adhered to the surface of the acoustic adjustment layer 54. The outer surface of the acoustic lens 55 is formed with a partial cylindrical surface. The partial cylindrical surface has a generatrix parallel to the second conductive film 31. The curvature of the partial cylindrical surface is determined according to the focal position of the ultrasonic waves emitted from one Xrow of elements 23 connected to one line of the first conductive films 29. The acoustic lens 55 is formed from silicone resin, for example.

A reinforcing plate 56 is fixed to the back surface of the base 21. The back surface of the base 21 is overlapped on the front surface of the reinforcing plate 56. The reinforcing plate 56 closes the openings 48 at the back surface of the element unit 17. The reinforcing plate 56 can be equipped with a rigid base. The reinforcing plate 56 can be formed from a silicon substrate, for example. The plate thickness of the base 21 is set to approximately 100 μm, for example, and the plate thickness of the reinforcing plate 56 is set to approximately 100 to 150 μm, for example. Here, the partition wall 49 is bonded to the reinforcing plate 56. The reinforcing plate 56 is bonded at a bonding area of at least one location on each partition wall 49. An adhesive agent can be used for the bonding.

Figure 5:
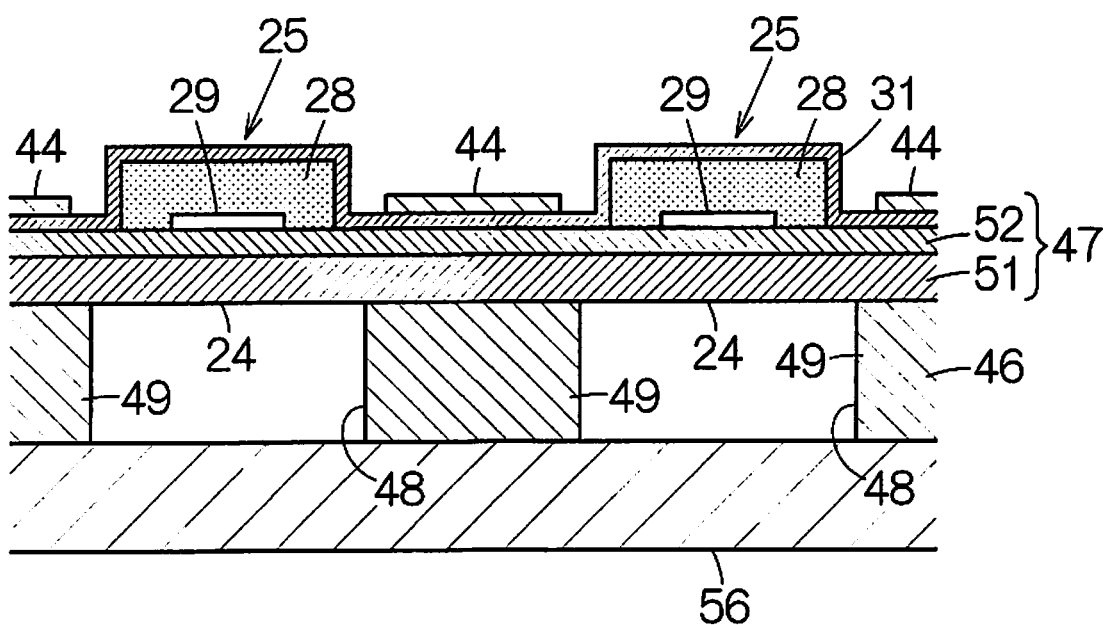
FIG. 5 is a partially enlarged cross section view along line B-B of FIG. 3.

As shown in FIG. 5, the piezoelectric film 28 is covered on the first conductive film 29. The piezoelectric film 28 contacts the surface of the vibration film 24 in a range expanding to the outside from the edge of the first conductive film 29. The piezoelectric film 28 completely separates the first conductive film 29 and the second conductive film 31 from each other. This avoids a short between the first conductive film 29 and the second conductive film 31.

The reinforcing body 43 (first elongated piece 44) is overlapped on the surface of the flexible film 47 on the partition wall 49. The first elongated piece 44 is overlapped on the partition wall 49 that functions as a girder to form a composite body. Depending on the overlapping, the composite body can have a second moment of area greater than the second moment of area of the base 21 alone. Here, with the composite body, the bending rigidity is increased in the direction orthogonal to the surface of the base 21.

(2) Operation of the Ultrasonic Diagnostic Device

Next, a brief description of the operation of the ultrasonic diagnostic device 11 will be provided. For sending of ultrasonic waves, pulse signals are supplied to the piezoelectric element 25 The pulse signals are supplied to the elements 23 for each Xrow through the lower electrode terminals 35 and 37 and the upper electrode terminals 34 and 36. With each element 23, an electric field acts on the piezoelectric film 28 between the lower electrode 27 and the upper electrode 26. The piezoelectric film 28 vibrates with the ultrasonic waves. The vibration of the piezoelectric film 28 is conveyed to the vibration film 24. In this way, the vibration film 24 does ultrasonic vibration. As a result, the desired ultrasonic beams are emitted toward the subject (e.g. the interior of a human body).

The reflected waves of the ultrasonic waves vibrate the vibration film 24. The ultrasonic vibration of the vibration film 24 makes the piezoelectric film 28 do ultrasonic vibration at a desired frequency. Voltage is output from the piezoelectric element 25 according to the piezoelectric effect of the piezoelectric element 25. Electric potential is generated between the upper electrode 26 and the lower electrode 27 with each element 23. The electric potential is output as electric signals from the lower electrode terminals 35 and 37 and the upper electrode terminals 34 and 36. In this way, ultrasonic waves are detected.

The sending and receiving of ultrasonic waves is repeated. As a result, linear scanning or sector scanning is realized. When scanning is completed, an image is formed based on the digital signals of the output signals. The formed image is displayed on the screen of the display panel 15.

With the element unit 17, the partition wall 49 forms a frame body that encloses the opening 48 for each of the openings 48. The first elongated piece 44 and the second elongated piece 45 are overlapped on the frame body to form a composite body. The bending rigidity of the composite body exceeds the bending rigidity of the frame body alone. The rigidity of the frame body is increased. Wobbling of the frame body during ultrasonic vibration of the vibration film 24 is suppressed. In this way, crosstalk of ultrasonic waves during ultrasonic vibration of one vibration film 24 is prevented. When the frame body rigidity is low, there is distortion of the frame body during ultrasonic vibration of the vibration film 24, and crosstalk of the ultrasonic waves from one vibration film 24 toward the adjacent vibration films 24 occurs.

The bending rigidity is specified by the product of the Young's modulus and the second moment of area. As described previously, if the second moment of area of the composite body formed by the partition wall 49 and the reinforcing body 43 is greater than the second moment of area of the partition wall 49 alone, the bending rigidity will increase. The reinforcing body 43 is able to effectively reinforce the bending rigidity.

In particular, the first elongated pieces 44 and the second elongated pieces 45 cross each other extending in the row direction and the column direction mutually crossing each other. By the first elongated pieces 44 and the second elongated pieces 45 crossing in a T shape or a plus shape, the rigidity of the reinforcing body 43 and thus the composite body is increased. In this way, the bending rigidity of the base 21 is further increased. Furthermore, since the crossing angle of the first elongated piece 44 and the second elongated piece 45 is set to 90 degrees, the bending rigidity of the base 21 is reliably increased in equal directions.

(3) Element Unit of the Second Embodiment

Figure 6:
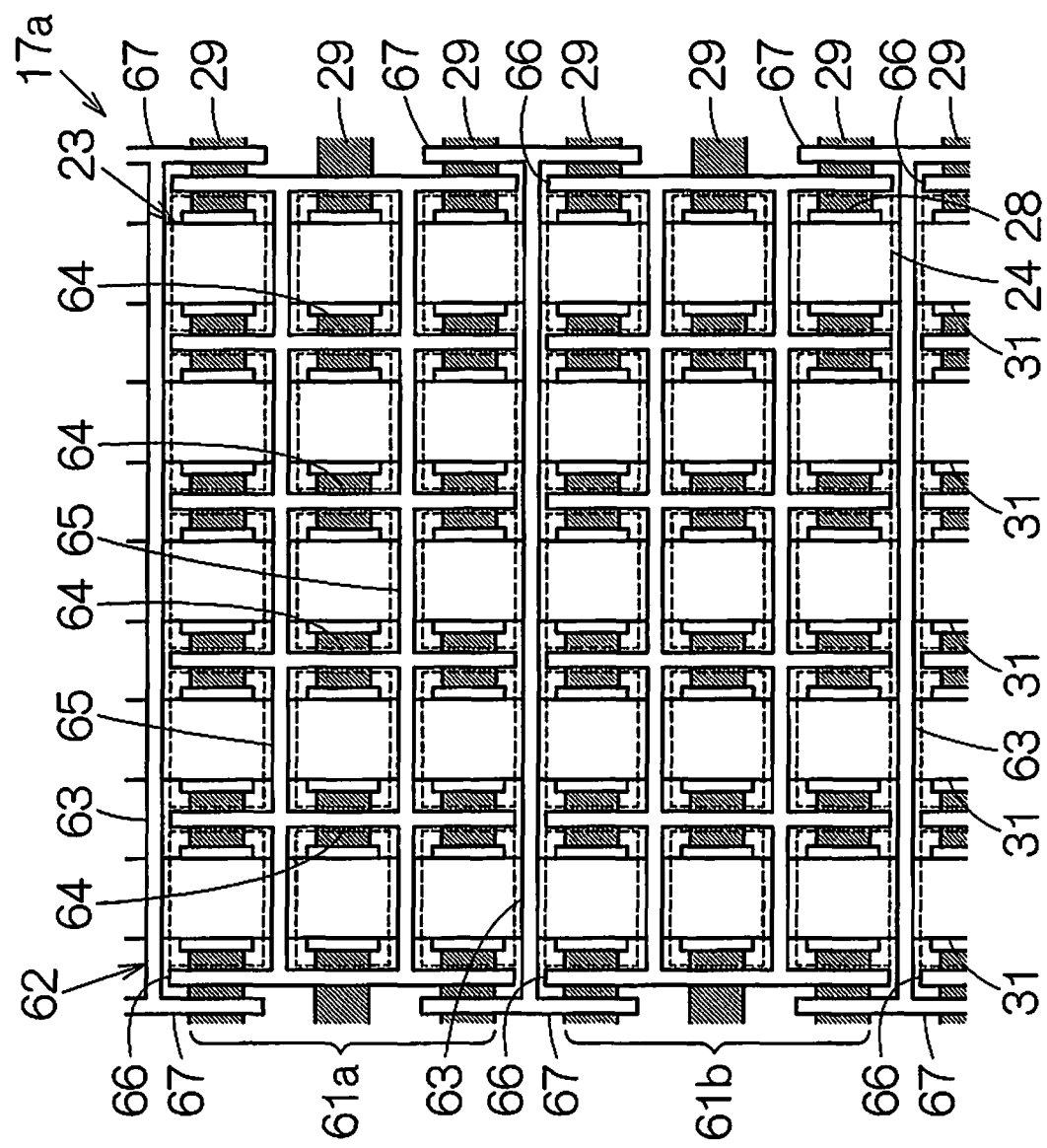
FIG. 6 is an enlarged partial plan view of the ultrasonic transducer element unit of the second embodiment, correlating to a partial enlarged view of FIG. 3.

FIG. 6 schematically shows the structure of an element unit 17a of the second embodiment. With this element unit 17a, one segment 61a, 61b, . . . is formed from a group of a plurality of Xrows of elements 23. In the drawing, one segment 61a and 61b is formed from the element 23 group connected in common to three lines of the first conductive films 29. The vibration films 24 belonging to one segment 61a and 61b vibrate simultaneously according to the supply of drive signals.

The reinforcing body 62 is equipped with a plurality of first elongated pieces (first straight line parts) 63 extending in the Xrow direction of the element array 22 (first direction) between the segments 61a and 61b, a plurality of second elongated pieces (second straight line parts) 64 arranged between adjacent elements 23 in the Xrow direction extending in the column direction of the element array 22 (second direction) within each segment 61a and 61b, and a plurality of third elongated pieces (first straight line parts) 65 arranged between adjacent elements 23 in the column direction extending in the Xrow direction of the element array 22 within each segment 61a and 61b. The first elongated pieces 63 and the third elongated pieces 65 are arranged in parallel to each other. The first elongated pieces 63 and the third elongated pieces 65 have a shape cutting across the area of the element array 22 in the column direction from one end to the other. The reinforcing body 62 has a plurality of crossing parts arranged separated in the column direction for each group of elements 23 connected in common to one signal line. The second elongated pieces 64 are interrupted for each segment 61a and 61b. At the boundary line of the segments 61a and 61b is formed a space 66 between the second elongated pieces 64. In this way, though they cross the third elongated pieces 65, the second elongated pieces 64 are separated by the space from the first elongated pieces 63 in the column direction. In this way, the reinforcing body 43 is segmented in the column direction for each group of elements 23 connected in common to one signal line. Since the reinforcing body 43 is interrupted for each segment 61a and 61b, transmission of ultrasonic vibration between the segments 61a and 61b conveyed through the reinforcing body 43 is prevented. Crosstalk of the ultrasonic waves is reduced.

Here, the first elongated pieces 63 pierce through the space 66 formed between the second elongated pieces 64. An auxiliary reinforcing body 67 extends in the column direction in parallel to the space 66 formed by segmenting of the second elongated pieces 64. The auxiliary reinforcing body 67 is overlapped on the surface of the flexible film 47, the same as the reinforcing body 62. The first elongated pieces 63 cross the auxiliary reinforcing body 67 in a T shape. In this way, the auxiliary reinforcing body 67 is connected to the first elongated pieces 63. As a result, even when the second elongated pieces 64 are segmented, the segmented areas are reinforced by the auxiliary reinforcing body 67. Despite the segmenting of the reinforcing body 62, it is possible to ensure rigidity by the working of the auxiliary reinforcing body 67. In addition, with the element unit 17a of this second embodiment, constitutions other than the constitution noted with the description above is the same as that of the element unit 17 of the first embodiment described above.

Figure 7:
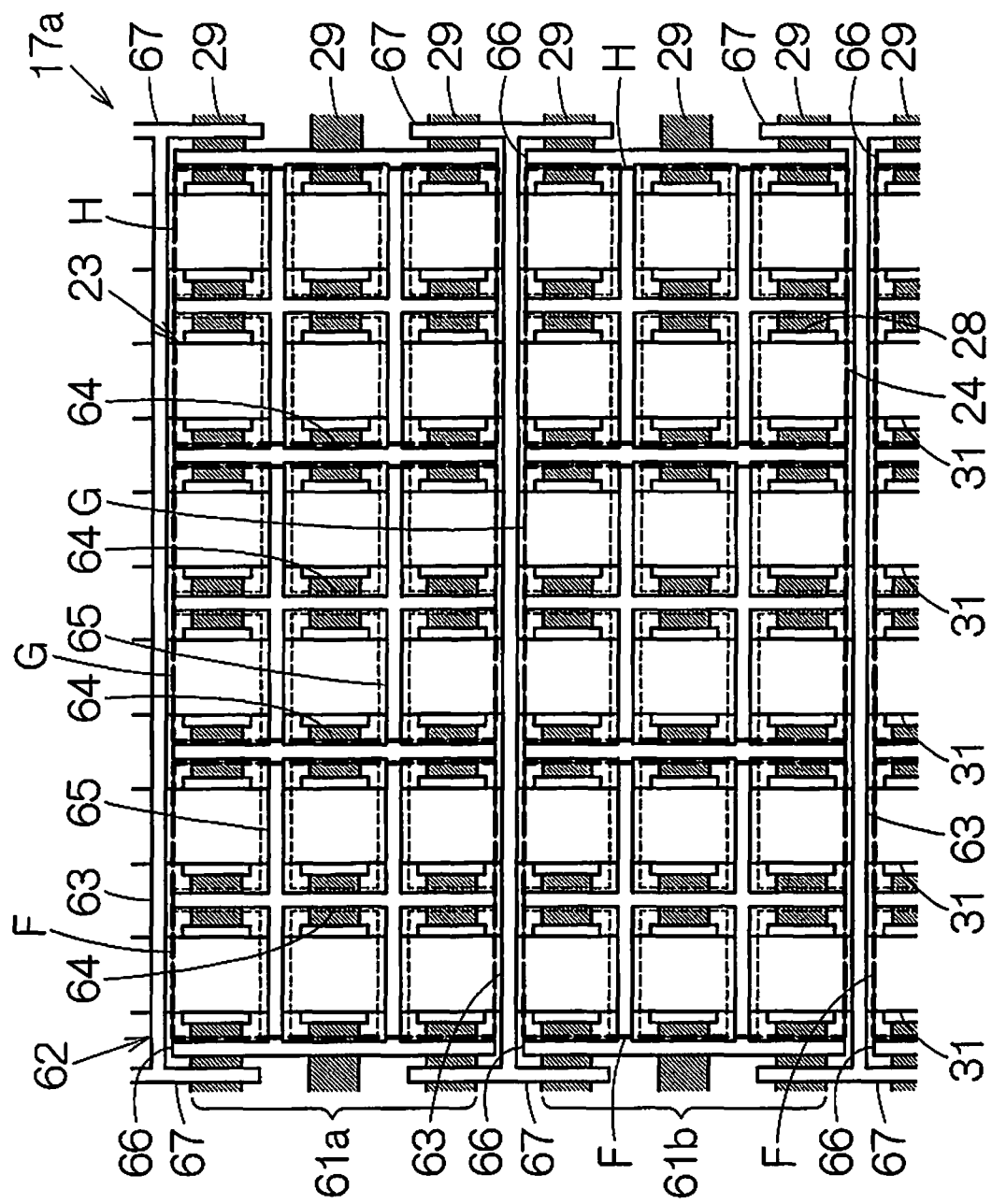
FIG. 7 is an enlarged partial plan view of the ultrasonic transducer element unit of a modification example of the second embodiment, correlating to the partial enlarged view of FIG. 3.

In addition, with the element unit 17a, as shown in FIG. 7, for example, it is also possible to further divide each segment 61a and 61b into smaller segments. Here, one segment 61a and 61b can respectively be divided into three small segments F, G, and H. When dividing, a common ground line is established for each two lines of second conductive films 31. In this way, small segments F, G, and H are formed for each group of elements 23 of two columns and three rows. The reinforcing body 62 has a plurality of crossing parts arranged separated in the first direction. The vibration films 24 belonging to each small segment F, G, and H vibrate simultaneously according to the supply of drive signals. The third elongated pieces 65 of the reinforcing body 62 are segmented for each group of elements 23 of two columns. In this way, the small segments F, G, and H can be arranged in array form.

(4) Element Unit of the Third Embodiment

Figure 8:
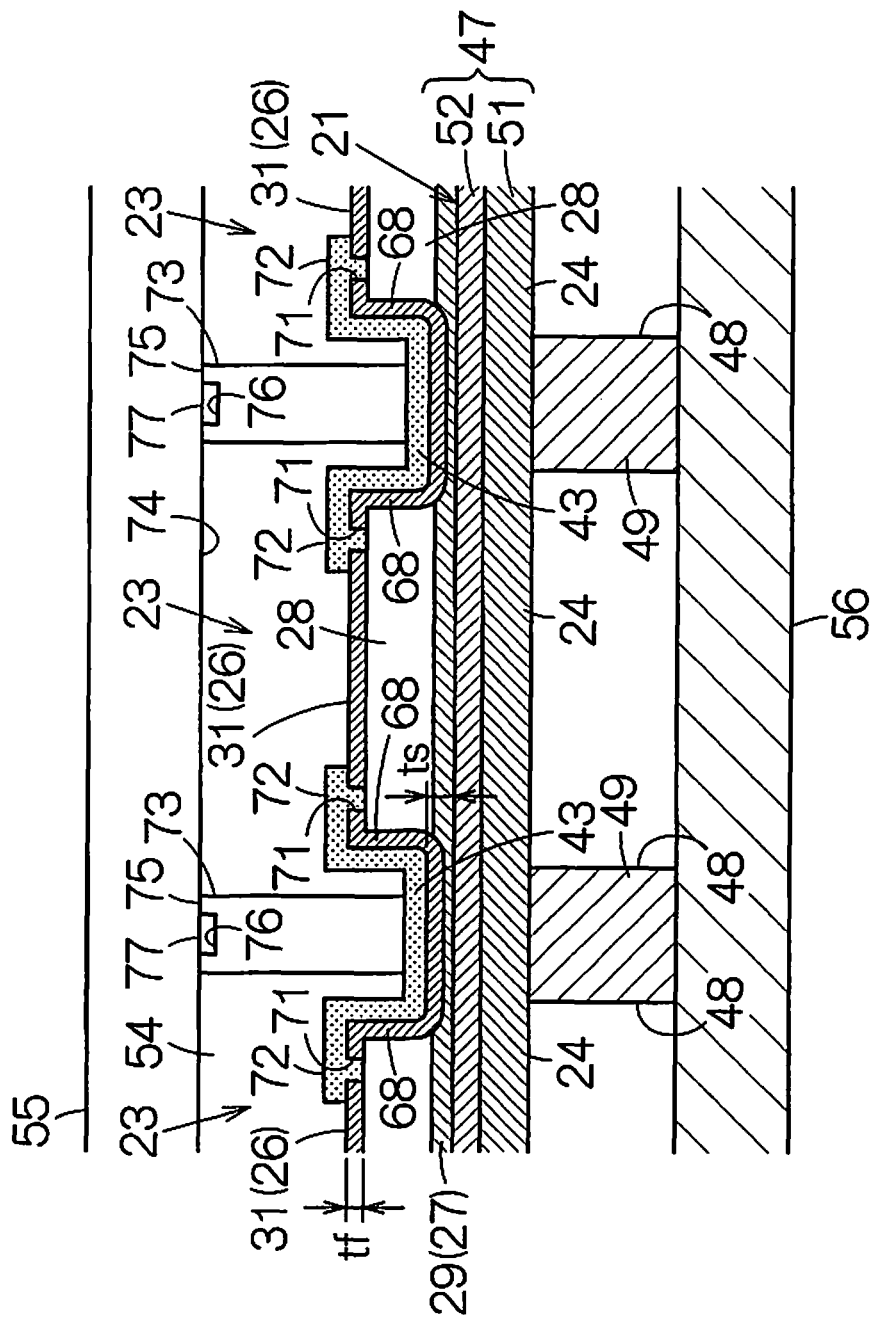
FIG. 8 is an enlarged partial cross section view of the ultrasonic transducer element unit of the third embodiment, correlating to the partial enlarged view of FIG. 4.

FIG. 8 schematically shows the structure of an element unit 17*b* of the third embodiment. With this element unit 17*b*, the film thickness ts of the second conductive film 41 increases between adjacent piezoelectric films 28. Between the piezoelectric films 28, the film thickness ts of the second conductive film 31 is greater than the film thickness tf of the first conductive film 29. Then, a protective conductive film 68 continues on the piezoelectric film 28 from the second conductive film 31 between the piezoelectric films 28. The protective conductive film 68 is covered on the side surface of the piezoelectric film 28. In this way, the protective conductive film 68 protects the side surface of the piezoelectric film 28 from dampness, for example.

A space 71 in contact with the piezoelectric film 28 is formed between the first conductive film 29 and the protective conductive film 68 on the piezoelectric film 28. The space 71 insulates the protective conductive film 68 from the first conductive film 29. The space 71 is occupied by an insulating film 72. Therefore, the protective conductive film 68 is separated from the first conductive film 29 by the insulating film 72. The insulating film 72 continues from the reinforcing body 43 (62). Specifically, the insulating film 72 is formed as a single unit on the reinforcing body 43 (62).

Here, a separating wall 73 is formed on the reinforcing body 43. The separating wall 73 is an object having greater acoustic impedance than the acoustic impedance of the acoustic adjustment layer 54, and is constituted from a solid having a Young's modulus that is greater than the Young's modulus of the acoustic adjustment layer 54. The separating wall 73 can be formed using a photoresist film hardened by heat, for example.

The acoustic lens 55 has a bonding surface 74 that expands within one plane. The acoustic lens 55 is adhered to the acoustic adjustment layer 54 and the top surface 75 of the separating wall 73 without interruption at the bonding surface 74. A cavity 76 that is recessed from the bonding surface with the acoustic lens 55 is formed on the top surface 75 of the separating wall 73. The space inside the cavity 76 is occupied by an adhesive layer 77. The top surface 75 of the separating wall 73 is bonded to the acoustic lens 55 by the adhesive layer 77. The adhesive layer 77 is formed using the same material as the acoustic adjustment layer 54.

The vibration film 24 does ultrasonic vibration with the sending of ultrasonic waves. The ultrasonic vibration is transmitted within the acoustic adjustment layer 54, and emitted from the interface of the acoustic adjustment layer 54. The ultrasonic vibration is transmitted across the interface to the acoustic lens 55. At this time, the separating wall 73 is formed between adjacent elements 23. An interface is formed on the acoustic adjustment layer 54 between adjacent elements 23 according to the difference in acoustic impedance. The interface prevents transmission of the ultrasonic vibration. As a result, the transmission of ultrasonic vibration from one vibration film 24 that does ultrasonic vibration toward the vibration film 24 of the adjacent element 23 is prevented. Ultrasonic wave crosstalk during ultrasonic vibration of one vibration film 24 is prevented.

The separating wall 73 is constituted using a solid having a Young's modulus greater than the Young's modulus of the acoustic adjustment layer 54. As a result, the rigidity of the acoustic adjustment layer 54 is reinforced by the separating wall 73. Crushing of the acoustic adjustment layer 54 in the thickness direction is prevented. The distance between the vibration film 24 and the interface of the acoustic adjustment layer 54 is kept constant. Ultrasonic waves can be radiated from the interface efficiently. At this time, the acoustic lens 55 is adhered to the surface of the acoustic adjustment layer 54 and the top surface 75 of the separating wall 73 by the bonding surface 74. Therefore, the acoustic lens 55 is supported by the separating wall 73. It is possible to reliably prevent crushing of the acoustic adjustment layer 54 in the thickness direction.

The surface of the acoustic adjustment layer 54 has the function of an adhesive agent. As a result, the acoustic lens 55 is adhered to the acoustic adjustment layer 54. Close adherence is maintained. Though the surface of the acoustic adjustment layers 54 layers is interrupted by the separating wall 73, the acoustic lens 55 is adhered to the top surface 75 of the separating wall 73 by the work of the adhesive layers 77. Even when the separating wall 73 is formed, a reduction in the acoustic lens 55 adherence area is kept to a minimum. In fact, when the acoustic lens 55 is bonded to the separating wall 73, it is possible for the acoustic lens 55 and the separating wall 73 to form a structure. The structure can even more reliably prevent deformation of the acoustic adjustment layer 54.

The cavity 76 is formed on the top surface 75 of the separating wall 73. The cavity 76 is occupied by the adhesive layer 77. The acoustic lens 55 is bonded to the top surface 75 of the separating wall 73 by the adhesive layer 77. At this time, the acoustic lens 55 is received on the top surface 75 of the separating wall 73. Therefore, the thickness of the acoustic adjustment layer 54 is determined by the position of the top surface 75 of the separating wall 73. The thickness of the acoustic adjustment layer 54 can be set with good precision according to the dimensional precision of the separating wall 73. In fact, the reduction in the adherence area of the acoustic lens 55 is kept to a minimum.

With the element unit 17*b*, the adhesive layer 77 is formed using the same material as the acoustic adjustment layer 54. Therefore, as described later, the adhesive layer 77 can be formed using the same manufacturing process as that of the acoustic adjustment layer 54. Having the manufacturing process become complex is avoided. Having the manufacturing cost increase is avoided.

Figure 9:
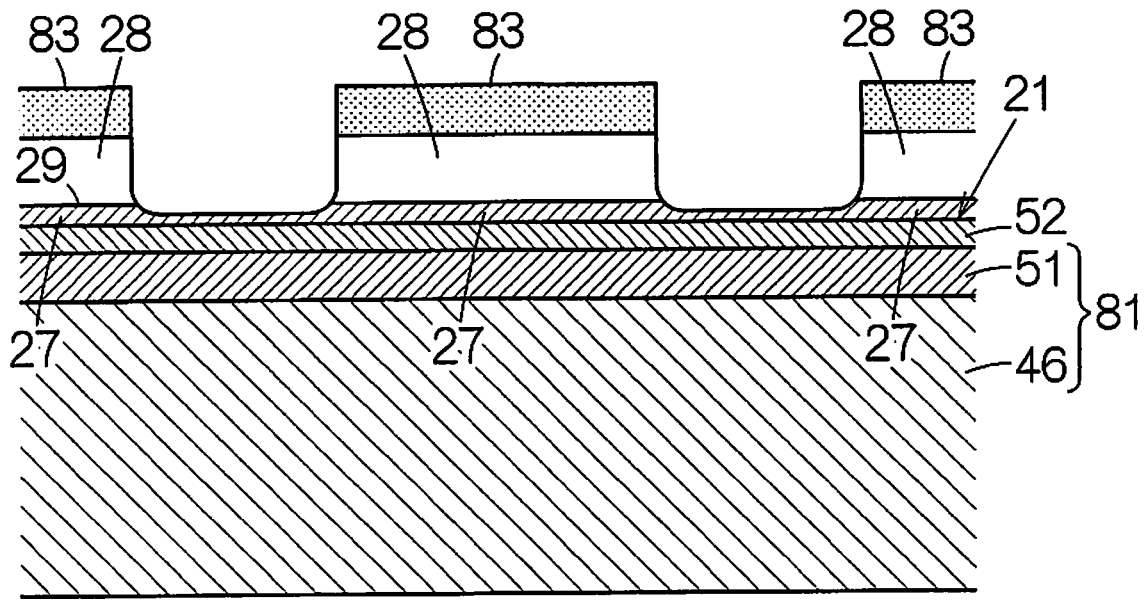
FIG. 9 is a drawing schematically showing the piezoelectric film forming process which is part of the manufacturing method of the ultrasonic transducer element unit.

Next, a brief description of the method of manufacturing the element unit 17*b* will be provided. A substrate 81 is prepared. The substrate 81 is formed from silicon, for example. On the surface of the substrate 81, for example, a heat treatment is implemented and an oxide film is formed. In this way, the main unit 46 and the silicon oxide layer 51 are formed from the substrate 81. On the surface of the silicon oxide layer 51, the zirconium oxide layer 52 is formed on the entire surface. On the surface of the zirconium oxide layer 52, the first conductive film 29 is formed. Photolithography technology can be used for forming these. Subsequently, the piezoelectric film 28 is formed on the zirconium oxide layer 52. As shown in FIG. 9, photolithography technology can similarly be used for forming this. The raw material film of the piezoelectric film 28 undergoes etching processing according to the pattern of a resist film. At this time, the first conductive film 29 is cut from the surface at a position separated from the resist film 83. The film thickness of the first conductive film 29 is reduced. In this way, the film thickness of the first conductive film 29 becomes smaller than the film thickness of the lower electrode 27. When the etching processing ends, the resist film 83 is removed.

Figure 10:
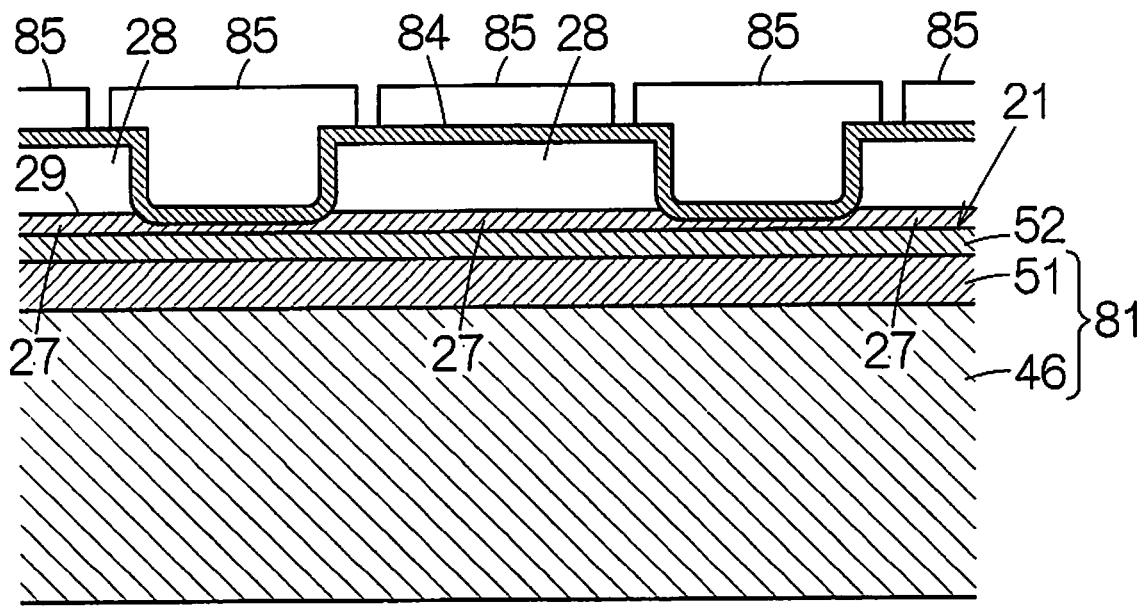
FIG. 10 is a drawing schematically showing the raw material layer forming process which is part of the manufacturing method of the ultrasonic transducer element unit.

Subsequently, the second conductive film 31 is formed on the zirconium oxide layer 52. As shown in FIG. 10, for formation of the second conductive film 31, a raw material film 84 is formed on the entire surface of the surface of the zirconium oxide layer 52. The raw material film 84 has a uniform film thickness. The raw material film 84 is formed from a conductive material. In this way, the raw material film 84 is covered at least on the exposed surface of the first conductive film 29 and the piezoelectric film 28. The film thickness of the first conductive film 29 increases. A resist film 85 is formed according to the designated pattern on the raw material film 84. For formation of the resist film 85, photolithography technology can be used, for example. The resist film 85 models the shape of the second conductive film 31.

Figure 11:
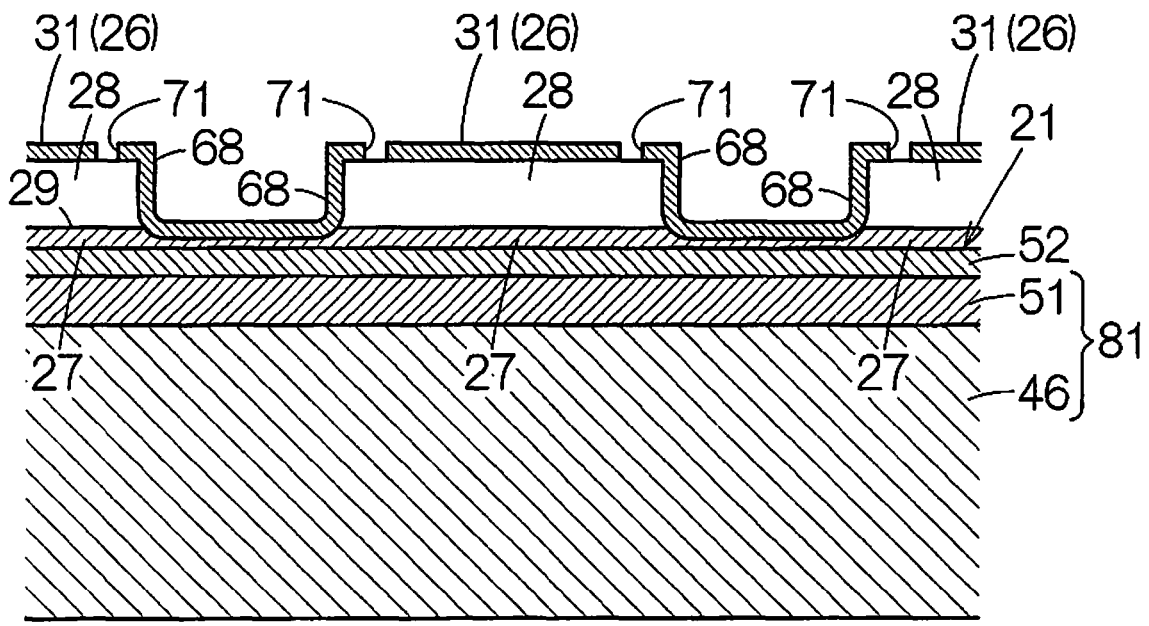
FIG. 11 is a drawing schematically showing the second conductive film forming process which is part of the manufacturing method of the ultrasonic transducer element unit.

As shown in FIG. 11, etching processing is implemented according to a designated pattern on the raw material film 84. The raw material film 84 is removed at a position separated from the resist film 85. In this way, the second conductive film 31 is formed from the raw material film 84. The outline of the upper electrode 26 is partitioned on the piezoelectric film 28. On the piezoelectric film 28, the protective conductive film 68 is formed separated from the upper electrode 26. The space 71 is formed on the raw material film 84. The protective conductive film 68 and the upper electrode 26 are separated by the space 71. When the etching processing ends, the resist film 85 is removed.

Figure 12:
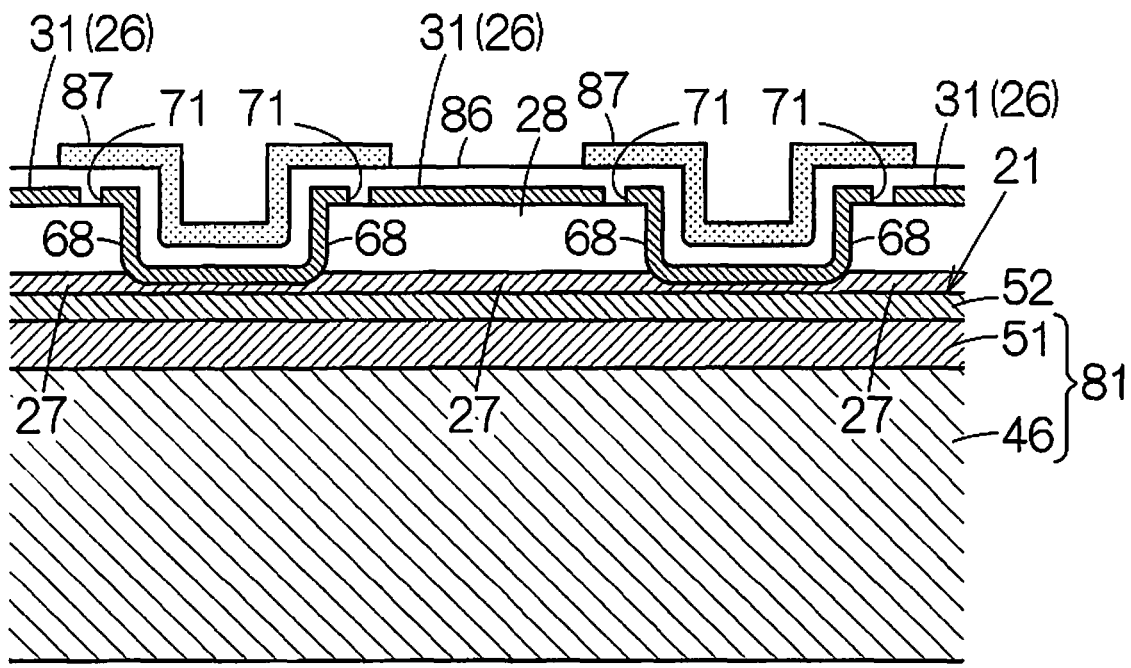
FIG. 12 is a drawing schematically showing the reinforcing body forming process which is part of the manufacturing method of the ultrasonic transducer element unit.

Subsequently, the reinforcing body 43 is formed on the zirconium oxide layer 52. As shown in FIG. 12, for forming the reinforcing body 43, the raw material film 86 is formed on the entire surface of the surface of the zirconium oxide layer 52. The raw material film 86 has a uniform film thickness. The raw material film 86 is formed from an insulating material. The raw material film 86 has a Young's modulus greater than the Young's modulus of the substrate 81. The raw material film 86 is filled into the space 71. The resist film 87 is formed according to a designated pattern on the raw material film 86. For forming of the resist film 87, photolithography technology can be used, for example. The resist film 87 models the shape of the reinforcing body 43.

Etching processing is implemented according to a designated pattern on the raw material film 86. The raw material film 86 is removed at a position separated from the resist film 87. In this way, the reinforcing body 43 (62) is formed from the raw material film 86. When the etching processing ends, the resist film 87 is removed. After that, the acoustic adjustment layer 54 is formed on the surface of the substrate 81. The openings 48 are formed on the back surface of the substrate 81. The vibration film 24 is established. The reinforcing plate 56 is adhered. In this way, the element unit 17b is manufactured.

With the manufacturing method of this embodiment, for formation of the piezoelectric film 28, etching processing was implemented. At this time, the first conductive film 29 is exposed to etching processing in the periphery of the piezoelectric film 28. As a result, the film thickness of the first conductive film 29 is reduced compared to the lower electrode 27. After that, the raw material film 84 is laminated on the first conductive film 29. In this way, the film thickness of the first conductive film 29 increases. It is possible to ensure sufficient film thickness for the wiring film connected to the lower electrode 27. It is possible to avoid an increase in wiring resistance. Therefore, it is possible to sufficiently ensure the ultrasonic wave detection sensitivity.

A detailed description of the embodiments was given as noted above, but a person skilled in the art will easily understand that it is possible to have many modifications without substantially straying from the novel items and effects of the present invention. Therefore, all of these kinds of modification examples are included within the scope of the present invention. For example, for terminology noted at least once together with a different term having a broader or the same meaning in the specification or drawings, that different terminology can be used as a substitute in any location in the specification or drawings. Also, the constitution and operation of the ultrasonic diagnostic device 11, the ultrasonic probe 13, the element units 17, 17a, and 17b, the elements 23, the piezoelectric elements 25 and the like are not limited to the items described with the embodiments, but can also have various modifications.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:
1. A diagnostic ultrasonic device comprising:
   a base including a partition wall defining a plurality of openings arranged in an array form;
   a flexible film in contact with a first side of the partition wall and including a plurality of vibration films;
   a reinforcing plate in contact with a second side of the partition wall;
   a plurality of ultrasonic transducer elements arranged respectively corresponding to the openings with the vibration films being respectively provided for the ultrasonic transducer elements, each of the ultrasonic transducer elements being constituted by a first conductive film, a piezoelectric film, and a second conductive film; and
   a reinforcing body fixed to the flexible film in an area between two adjacent vibration films when viewed along a thickness direction of the base, the reinforcing body having Young's modulus greater than Young's modulus of the base, a thickness of the reinforcing body being smaller than a thickness of each of the ultrasonic transducer elements.

2. The ultrasonic device according to claim 1, wherein the reinforcing body, in cooperation with the base, forms a composite body having a second moment of area greater than a second moment of area of the base alone.

3. The ultrasonic device according to claim 2, wherein the reinforcing body has a crossing part along a first direction and a second direction that cross each other when viewed along the thickness direction of the base.

4. The ultrasonic device according to claim 3, wherein a crossing angle of the first direction and the second direction is 90 degrees.

5. The ultrasonic device according to claim 3, wherein when viewed along the thickness direction of the base, the reinforcing body has a first straight line part cutting across an array area of the ultrasonic transducer elements in the first direction.

6. The ultrasonic device according to claim 3, wherein the reinforcing body has an additional crossing part spaced apart from the crossing part in the second direction for each group of the ultrasonic transducer elements connected in common to one signal line among the ultrasonic transducer elements.

7. The ultrasonic device according to claim 6, wherein the reinforcing body further includes a first straight line part positioned in an area between the crossing part and the additional crossing part when viewed along the thickness direction of the base, and an auxiliary reinforcing body part extending along the second direction.

8. The ultrasonic device according to claim 5, wherein the reinforcing body has a second straight line part cutting across the array area of the ultrasonic transducer elements in the second direction when viewed along the thickness direction of the base.

9. The ultrasonic device according to claim 5, wherein the reinforcing body has an additional crossing part spaced apart from the crossing part in the first direction for each group of the ultrasonic transducer elements connected in common to one signal line among the ultrasonic transducer elements.

10. The ultrasonic device according to claim 1, further comprising:
a first conductive film extending in a first direction in common to the ultrasonic transducer elements;
a piezoelectric film disposed on the first conductive film for each of the ultrasonic transducer elements;
a second conductive film extending in a second direction in common to the ultrasonic transducer elements; and
an insulating film separating the first conductive film from the second conductive film on the piezoelectric film, the insulating film being continuous from the reinforcing body, wherein
the reinforcing body is made of an insulating material.

11. The ultrasonic device according to claim 10, further comprising
an additional second conductive film extending in the second direction, wherein
the first conductive film has a film thickness greater than a film thickness of the second conductive film between the second conductive film and the additional second conductive film.

12. A probe comprising:
the ultrasonic device according to claim 1; and
a case supporting the ultrasonic device.

13. An electronic equipment comprising:
the ultrasonic device according to claim 1; and
a processing device connected to the ultrasonic device, and configured to process output of the ultrasonic device.

14. An ultrasonic image device comprising:
the ultrasonic device according to claim 1; and
a display device configured to display an image generated based on output of the ultrasonic device.

15. The ultrasonic device according to claim 1, wherein the plurality of vibration films are disposed between the plurality of ultrasonic transducer elements and a corresponding opening of the plurality of openings.

16. The ultrasonic device according to claim 1, wherein the reinforcing body is arranged not to overlap the ultrasonic transducer elements when viewed along the thickness direction of the base.

* * * * *